though condensation of an ylidene-β-ketocarboxylic

United States Patent [19]

Meyer et al.

[11] 3,933,834

[45] Jan. 20, 1976

[54] UNSYMMETRICAL ESTERS OF N-SUBSTITUTED 1,4-DIHYDROPYRIDINE 3,5-DICARBOXYLIC ACID

[75] Inventors: Horst Meyer, Wuppertal; Friedrich Bossert, Wuppertal-Elberfeld; Wulf Vater, Opladen; Kurt Stoepel, Wuppertal, all of Germany

[73] Assignee: Bayer Aktiengesellschaft, Germany

[22] Filed: Aug. 13, 1974

[21] Appl. No.: 496,972

Related U.S. Application Data

[63] Continuation-in-part of Ser. No. 336,605, Feb. 28, 1973, Pat. No. 3,883,540.

[30] Foreign Application Priority Data

June 3, 1972   Germany............................ 2210672

[52] U.S. Cl................. 260/294.8 D; 260/294.8 C; 260/294.8 F; 260/294.8 G; 260/294.9; 260/295.5 R; 260/295.5 B; 424/266

[51] Int. Cl.²....................................... C07D 213/55

[58] Field of Search............... 260/295.5 R, 294.8 D

[56] References Cited

UNITED STATES PATENTS 3,773,773   11/1973   Bossert ....................... 260/294.8 D Primary Examiner—Alan L. Rotman

[57] ABSTRACT

Unsymmetrical esters of N-substituted 4-substituted-1,4-dihydropyridine 3,5-dicarboxylic acid substituted in the 4-position by pyridyl, thienyl, furyl and pyrryl and optionally substituted in the 2- and 6-positions by lower alkyl. The products can be prepared (A) through condensation of an ylidene-β-ketocarboxylic acid ester, with a β-ketocarboxylic acid ester and an amine or salt thereof, or with an enamino carboxylic acid ester or (B) through condensation of an aldehyde, an enamino carboxylic acid ester and a β-ketocarboxylic acid ester. The said products have utility as cardiovascular agents.

11 Claims, No Drawings

UNSYMMETRICAL ESTERS OF N-SUBSTITUTED 1,4-DIHYDROPYRIDINE 3,5-DICARBOXYLIC ACID

This application is a continuation-in-part of U.S. Ser. No. 336,605, filed Feb. 28, 1973, now U.S. Pat. No. 3,883,540.

The present invention relates to certain new unsymmetrical N-substituted 1,4-dihydropyridinedicarboxylic acid esters, to processes for their production, and to their use as coronary and anti-hypertensive agents.

It has already been disclosed that N-alkyl 1,4-dihydropyridines are obtained by reaction of 1,5-diketones with alkylamines (Merz, Richter, Arch. Pharm. 275, 294 (1937). A known variant of this process consists in the reaction of aldehydes with β-dicarbonyl compounds and amine hydrochlorides according to German Offenlegungschrift 1,923,990. Symmetrical 1,4-dihydropyridine derivatives were produced by these methods. Until the present invention, it has not been possible to produce unsymmetrical esters of the N-substituted 1,4-dihydropyridines and such esters have hitherto not been disclosed.

The present invention relates to unsymmetrical 1,4-dihydropyridinecarboxylic acid esters of the general formula:

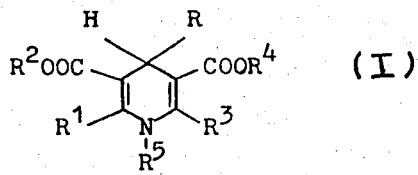

in which

R is mono-, di- or trisubstituted phenyl, in which the substituents are selected from the group consisting of nitro, cyano, azido and $S(O)_n$-lower alkyl, wherein $n = 0$, 1 or 2, lower alkyl, lower alkoxy and halogeno, the total number of said substituents being not more than 3 and at least one of said substituents being nitro, cyano, azido or $S(O)_n$-lower alkyl; or R is an aromatic ring system selected from the group consisting of naphthyl, quinolyl and isoquinolyl; or R is a heterocyclic ring system selected from the group consisting of pyridyl, pyrimidyl, thienyl, furyl and pyrryl, said aromatic ring system and said heterocyclic ring system being unsubstituted or substituted by at least one lower alkyl, lower alkoxy or halogeno;

$R^1$ and $R^3$, independent of the other, is hydrogen or lower alkyl;

$R^2$ and $R^4$ are different from one another and are lower alkyl, lower alkenyl, lower alkynyl, lower alkoxy(-lower alkyl) or lower cycloalkyl, unsubstituted or substituted by hydroxy;

$R^5$ is lower alkyl or benzyl.

The term lower alkyl denotes a univalent saturated branched or straight hydrocarbon chain containing from 1 to 6 carbon atoms as, for example, methyl and hexyl.

The term lower alkenyl denotes a univalent branched or straight hydrocarbon chain containing from 2 to 6 carbon atoms and ethylenic unsaturation as, for example, vinyl and 4-hexenyl.

The term lower alkynyl denotes a univalent branched or straight hydrocarbon chain containing from 2 to 6 carbon atoms and acetylenic unsaturation as, for example, ethynyl and 5-hexynyl.

The term lower denotes denotes a straight or branched hydrocarbon chain bound to the remainder of the molecule through an ethereal oxygen atom as, for example, methoxy and hexoxy.

The term halogeno cdenotes the substituents fluoro, chloro, bromo and iodo.

The term lower cycloalkyl denotes a univalent cyclic hydrocarbon ring having 3 to 6 carbon atoms, as for example, cyclopropyl, cyclobutyl, cyclopentyl and cyclohexyl, and the like.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitic acid, salicyclic acid, phthalic acid, embonic acid, enanthic acid, and the like.

The compounds of the present invention can exist as optical isomers and both the racemates of these isomers and the individual isomers themselves are within the scope of the present invention. The racemates can be separated into their individual isomers through the well-known technique and forming diastereoisomeric salts with optically active acids.

In the general formula I, above, the present invention may be more particularly defined as follows:

R is phenyl radical substituted by 1 or 2 nitro, especially one nitro, or by one cyano, azido or $S(O)_n$-lower alkyl, where n is 0 or 2, particularly of 1 to 4 carbon atoms, and which may also be substituted by lower alkyl or lower alkoxy, particularly of 1 to 4 carbon atoms and alkyl or lower alkoxy, particularly of 1 to 4 carbon atoms and more particularly of 1 or 2 carbon atoms, and/or by halogen, particularly chlorine or bromine, with the total number of the substituents being at most 3, preferably 2, or R is naphthyl, quinolyl, isoquinolyl, thienyl or furyl, which is unsubstituted or substituted by lower alkyl or lower alkoxy, particularly of 1 to 4 carbon atoms or by chlorine or bromine;

$R^1$ and $R^3$ are hydrogen or lower alkyl, particularly of 1 to 4 carbon atoms, and more particularly of 1 or 2 carbon atoms;

$R^2$ and $R^4$ are different from one another and are lower alkyl, lower alkenyl, lower alkynyl, lower alkoxy(-lower alkyl), particularly of up to 4 carbon atoms in each moiety, or cyclohexyl, which may be substituted by hydroxy; and $R^5$ is lower alkyl, particularly of 1 to 4 carbon atoms, and more particularly of 1 to 3 carbon atoms, or benzyl.

The new compounds may be prepared as follows:

a. a ylidene-β-ketocarboxylic acid ester of the general formula:

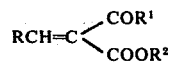

is reacted with a β-ketocarboxylic acid ester of the general formula:

and with an amine of the general formula:

R⁵NH₂ or a salt thereof, if appropriate with intermediate isolation of the N-substituted enaminocarboxylic acid ester of the general formula:

or
b. an aldehyde of the general formula

RCHO is reacted with an enaminocarboxylic acid ester of the general formula:

and a β-ketocarboxylic acid ester of the general formula:

R³COCH₂COOR⁴ in water or an inert organic solvent;
in which R, R¹, R², R³, R⁴ and R⁵ are as defined above.

The two modes (a) and (b) described above of effecting the process of the invention will hereinafter be referred to as "Process Variants" (a) and (b).

If 3'-nitrobenzylideneacetoacetic acid methyl ester and either N-methylaminocrotonic acid isopropyl ester or acetoacetic acid isopropyl ester and methylamine are used as the starting materials, the course of the reaction of Process Variant (a) can be represented by the following equation:

If 3-nitrobenzaldehyde, acetoacetic acid ethyl ester and N-methylaminocrotonic acid isopropyl ester are used as the starting materials, the following equation illustrates Process Variant (b):

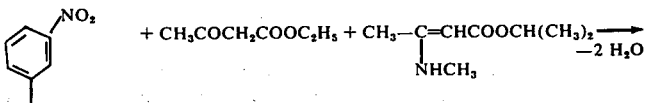

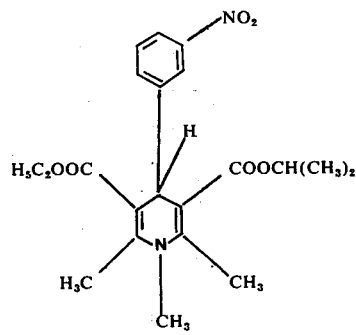

The starting materials used to prepare the compounds of the invention are known or can readily be produced by known methods.

The ylidene-β-ketocarboxylic acid esters are known or can be produced by known methods (org. Reactions XV, 204 ff, (1967)).

As examples there may be mentioned:

Ylidene-β-ketocarboxylic acid esters

2'-nitrobenzylideneacetoacetic acid methyl ester,
2'-nitrobenzylideneacetoacetic acid ethyl ester,
3'-nitrobenzylideneacetoacetic acid ethyl ester,
3'-nitrobenzylideneacetoacetic acid methyl ester,
3'-nitrobenzylideneacetoacetic acid isopropyl ester,
3'-nitrobenzylideneacetoacetic acid allyl ester,
3'-nitrobenzylideneacetoacetic acid propargyl ester,
3'-nitrobenzylideneacetoacetic acid β-methoxy-ethyl ester,
3'-nitrobenzylideneacetoacetic acid cyclohexyl ester,
3'-nitrobenzylidenepropionylacetic acid ethyl ester,
2'-cyanobenzylideneacetoacetic acid methyl ester,
2'-cyanobenzylideneacetoacetic acid ethyl ester,
2'-cyanobenzylideneacetoacetic acid propyl ester,
2'-cyanobenzylideneacetoacetic acid β-n-propoxyethyl ester,
4'-nitrobenzylideneacetoacetic acid methyl ester,
3'-cyanobenzylideneacetoacetic acid methyl ester,
4'-cyanobenzylideneacetoacetic acid ethyl ester,
3'-nitro-4'-chlorobenzylideneacetoacetic acid t-butyl ester,

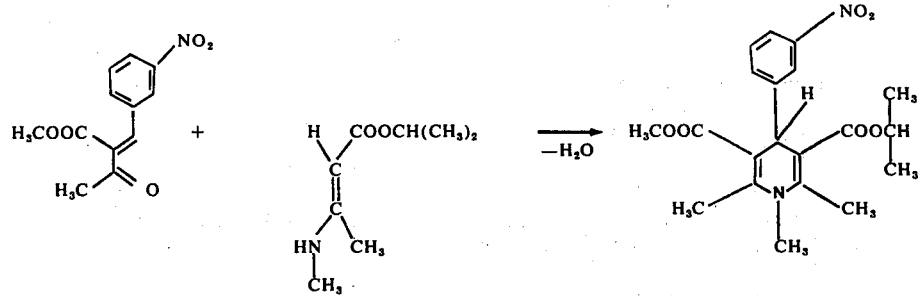

3'-nitro-6'-chlorobenzylideneacetoacetic acid ethyl ester,
3'-nitro-4'-methoxybenzylideneacetoacetic acid methyl ester,
2'-nitro-4'-methoxybenzylideneacetoacetic acid methyl ester,
2'-cyano-4'-methylbenzylideneacetoacetic acid ethyl ester,
4'-methylmercaptobenzylideneacetoacetic acid ethyl ester,
2'-methylmercaptobenzylideneacetoacetic acid methyl ester,
2'-sulphinylmethylbenzylideneacetoacetic acid isopropyl ester,
2'-sulphonylmethylbenzylideneacetoacetic acid ethyl ester,
(1'-naphthylmethylidene)-acetoacetic acid methyl ester,
2'-ethoxy-(1'-naphthylmethylidene)-acetoacetic acid ethyl ester,
5'-bromo-(1'-naphthylmethylidene)-acetoacetic acid methyl ester,
(2'-quinolyl)-methylideneacetoacetic acid ethyl ester,
(8'-quinolyl)-methylideneacetoacetic acid methyl ester,
(1'-isoquinolyl)-methylideneacetoacetic acid ethyl ester,
(3'-isoquinolyl)-methylideneacetoacetic acid isopropyl ester,
α-pyridylmethylideneacetoacetic acid methyl ester,
α-pyridylmethylideneacetoacetic acid ethyl ester,
α-pyridylmethylideneacetoacetic acid cyclohexyl ester,
β-pyridylmethylideneacetoacetic acid β-ethoxyethyl ester,
6-methyl-α-pyridylmethylideneacetoacetic acid ethyl ester,
4',6'-dimethoxy-(5'-pyrimidyl)-methylideneacetoacetic acid ethyl ester,
2'thenylideneacetoacetic acid ethyl ester,
2'-furfurylideneacetoacetic acid ethyl ester,
(2'-pyrryl)-methylideneacetoacetic acid methyl ester and
α-pyridylmethylidene propionylacetic acid ethyl ester.

The β-ketocarboxylic acid esters are known or can be produced by known methods (Pohl and Schmidt, U.S. Pat. No. 2,351,366 (1940), ref. in Chemical Abstracts 1944, 5224).
As examples there may be mentioned:

β-Ketocarboxylic acid esters

Formylacetic acid ethyl ester,
acetoacetic acid methyl ester,
acetoacetic acid ethyl ester,
acetoacetic acid propyl ester,
acetoacetic acid isopropyl ester,
acetoacetic acid 6-butyl ester,
acetoacetic acid butyl ester,
acetoacetic acid (α- or β-)methoxyethyl ester,
acetoacetic acid (α- or β-)propoxyethyl ester,
acetoacetic acid (α- or β-)hydroxyethyl ester,
acetoacetic acid allyl ester,
acetoacetic acid propargyl ester,
acetoacetic acid cyclohexyl ester,
propionylacetic acid ethyl ester,
butyrylacetic acid methyl ester, and
isobutyrylacetic acid ethyl ester.

The amines of general formula $R^5NH_2$ are known.

As examples there may be mentioned:
Methylamine, ethylamine, propylamine, isopropylamine, butylamine, isobutylamine and benzylamine.
The N-substituted enaminocarboxylic acid esters are known or can be produced by known methods (A.C. Cope, J.A.C.S. 67, 1017 (1945)).
As examples there may be mentioned:

N-Substituted enaminocarboxylic acid esters

β-N-Methylaminocrotonic acid methyl ester,
β-N-methylaminocrotonic acid ethyl ester,
β-N-methylaminocrotonic acid isopropyl ester,
β-N-ethylaminocrotonic acid ethyl ester,
β-N-isopropylaminocrotonic acid methyl ester,
β-N-methylaminocrotonic acid β-methoxyethyl ester,
β-N-methylaminocrotonic acid cyclohexyl ester,
β-N-methylamino-β-ethylacrylic acid ethyl ester and
β-N-benzylaminocrotonic acid ethyl ester.

The aldehydes of general formula RCHO are known or can be produced by known methods (E. Mosettig, Org. Reactions VIII, 218 ff. (1954)).
As examples there may be mentioned:
2-, 3- or 4-Nitrobenzaldehyde,
2,4- or 2,6-dinitrobenzaldehyde,
2-nitro-6-bromobenzaldehyde,
2-nitro-3-methoxybenzaldehyde,
2-nitro-3-methoxy-6-chlorobenzaldehyde,
2-nitro-4-methoxybenzaldehyde,
3-nitro-6-chlorobenzaldehyde,
2-, 3- or 4-cyanobenzaldehyde,
α-, β- or γ-pyridinaldehyde,
6-methylpyridin-2-aldehyde,
pyrimidin-5-aldehyde,
4,6-dimethoxy-pyrimidin-5-aldehyde,
2-methylmercaptobenzaldehyde,
2-methylsulphonylbenzaldehyde,
2-methylsulphinylbenzaldehyde,
1- and 2-naphthaldehydes,
5-bromo-1-naphthaldehyde,
2-ethoxy-1-naphthaldehyde,
4-methyl-1-naphthaldehyde,
quinolin-2-, 3-, 4-, 5-, 6-, 7- and 8-aldehydes,
isoquinolin-1- and 3-aldehydes,
furan-2-aldehyde,
thiophen-2-aldehyde and
pyrrol-2-aldehyde.

Possible solvents for use in the process of the invention are water and all inert organic solvents. Preferably, the solvents are alcohols, such as ethanol and methanol, ethers, such as dioxane and diethyl ether, glacial acetic acid, dimethylformamide, dimethylsulphoxide, acetonitrile and pyridine.

The reaction temperatures can be varied within a substantial range. In general, the reaction is carried out at between 20° and 200°C, preferably at the boiling point of the solvent.

The reaction can be carried out under normal pressure but also at elevated pressure. In general, normal pressure is used.

In carrying out the process according to the invention, the substances participating in the reaction are each employed in approximately stoichiometric amounts, except that in Process Variant (a), the amine or its salt which is used is appropriately added in an excess of 1 to 2 mols.

Typical compounds of the invention are:
1-methyl-4-(2'-nitrophenyl)-1,4-dihydropyridine-3,5-dicarboxylic acid 3-methyl-ester-5-isopropyl-ester.
1,2,6-trimethyl-4-(2'-nitrophenyl)-1,4-dihydropyridine-3,5-dicarboxylic acid 3-methyl-ester-5-isopropyl-ester.

1,2,6-trimethyl-4-(3'-nitrophenyl)-1,4-dihydropyridine-3,5-dicarboxylic acid 3-methyl-ester-5-ethyl-ester.

1,2,6-trimethyl-4-(3'-nitrophenyl)-1,4-dihydropyridine-3,5-dicarboxylic acid 3-ethyl-ester-5-isopropyl-ester.

1,2,6-trimethyl-4-(3'-nitrophenyl)-1,4-dihydropyridine-3,5-dicarboxylic acid 3-ethyl-ester-5-allyl-ester.

1,2,6-trimethyl-4-(3'-nitrophenyl)-1,4-dihydropyridine-3,5-dicarboxylic acid 3-methyl-ester-5-β-methoxyethylester.

1-benzyl-2,6-dimethyl-4-(3'-nitrophenyl)-1,4-dihydropyridine-3,5-dicarboxylic acid 3-methyl-ester-5-ethyl-ester.

1,2,6-trimethyl-4-(3'-nitrophenyl)-1,4-dihydropyridine-3,5-dicarboxylic acid 3-methyl-ester-5-cyclohexyl-ester.

1,6-dimethyl-2-ethyl-4-(3'-nitrophenyl)-1,4-dihydropyridine-3,5-dicarboxylic acid 3-ethyl-ester-5-isopropyl-ester.

1,2,6-trimethyl-4-(2'-cyanophenyl)-1,4-dihydropyridine-3,5-dicarboxylic acid 3-methyl-ester-5-ethyl-ester.

1,2,6-trimethyl-4-(2'-cyanophenyl)-1,4-dihydropyridine-3,5-dicarboxylic acid 3-ethyl-ester-5-allyl-ester.

1,2,6-trimethyl-4-(2'-cyanophenyl)-1,4-dihydropyridine-3,5-dicarboxylic acid 3-ethyl-ester-5-isopropyl-ester.

1,6-dimethyl-2-ethyl-4-(2'-cyanophenyl)-1,4-dihydropyridine-3,5-dicarboxylic acid 3-ethyl-ester-5-methyl-ester.

1-benzyl-2,6-dimethyl-4-(2'-cyanophenyl)-1,4-dihydropyridine-3,5-dicarboxylic acid 3-methyl-ester-5-ethyl-ester.

1,2,6-trimethyl-4-(3'-nitro-6'-chlorophenyl)-1,4-dihydropyridine-3,5-dicarboxylic acid 3-ethyl-ester-5-isopropyl-ester.

1,2,6-trimethyl-4-(3'-nitro-6'-chlorophenyl)-1,4-dihydropyridine-3,5-dicarboxylic acid 3-ethyl-ester-5-β-methoxyethylester.

1,2,6-trimethyl-4-(furyl-2')-1,4-dihydropyridine-3,5-dicarboxylic acid 3-methyl-ester-5-ethyl-ester.

1-benzyl-2,6-dimethyl-4-(furyl-2')-1,4-dihydropyridine-3,5-dicarboxylic acid 3-methyl-ester-5-isopropyl-ester.

1,2,6-trimethyl-4-(2'-pyridyl)-3-carbethoxy-5-carboxypropoxy-1,4-dihydropyridine.

1-butyl-2,6-diethyl-4-(3'-pyridyl)-3-carbomethoxy-5-carbo-β-methoxyethoxy-1,4-dihydropyridine.

1,2-dimethyl-6-ethyl-4-(3'-pyridyl)-3-carbomethoxy-5-carboisopropoxy-1,4-dihydropyridine.

1-isopropyl-2,6-dimethyl-4-(thienyl-2')-3-carbomethoxy-5-carboethoxy-1,4-dihydropyridine.

1,2,6-trimethyl-4-(furyl-2')-3-carboisopropoxy-5-carbo-β-propoxyethoxy-1,4-dihydropyridine.

1,2,6-trimethyl-4-(furyl-2')-3-carboethoxy-5-carboisopropoxy-1,4-dihydropyridine.

As noted above, the compounds of the present invention demonstrate the ability to reduce blood pressure and to effect a dilation of the coronary vessels. They can accordingly be used where either or both of these effects are desired. Thus upon parenteral, oral or sublingual administration, the compounds produce a distinct and long lasting dilation of the coronary vessels which is intensified by a simultaneous nitrite-like effect of reducing the load on the heart. In their strength of action, the compounds of the invention are superior to the known symmetrical N-substituted dihydropyridinedicarboxylic acid esters. The effect on heart metabolism is thus one of energy saving. In addition, the compounds lower the blood pressure of normotonic and hypertonic animals and can thus be used as antihypertensive agents. These properties can be conveniently observed in well known laboratory models. Thus, for example, the coronary vessel dilation effect of the compounds of the invention was compared with the action of Persantin by measuring the rise in oxygen saturation in the coronary sinus in the narcotized, heart-catheterized dog, with the results reported in Table I, below.

Table I

| Compound | Dose mg/kg.[1] | O₂% Rise [2] | Reversion time [3] |
|---|---|---|---|
| Example 2 | 0.01 | 31 | >3.5 |
| Example 3 | 0.1 | 39 | >6 |
| Example 6 | 0.05 | 39 | >4 |
| Persantin | 0.3 | 23 | 1–2 |
| do. | 0.4 | 34 | 1–2 |

Notes
[1] Dose given in mg/kg. body weight, administered intravenously;
[2] $O_2$ rise given as % rise in oxygen saturation;
[3] Reversion time given is time in hours for reversion to the initial value.

The hypotensive activity of the present compounds can be observed by measuring the blood pressure of hypertensive rats following administration of the compounds. Table II below demonstrates the lowest dose which results in at least a 15 mm Hg reduction in blood pressure of such animals.

Table II

| Compound | Peroral Dose (mg/kg) |
|---|---|
| Example 1 | 0.3 |
| Example 2 | 1.0 |
| Example 3 | 0.3 |
| Example 6 | 0.3 |

The toxicity of the present compounds is favorable, as demonstrated by the data in Table III below, which reports the $LD_{50}$ as measured on mice by peroral administration.

Table IV

| Compound | $LD_{50}$ (mg/kg) |
|---|---|
| Example 1 | 3000 |
| Example 2 | 3000 |
| Example 3 | 3000 |

In addition to the effect on blood pressure and coronary vessels, the compounds also lower the excitability of the stimulus formation and excitation conduction system within the heart so that an antifibrillation action is observed at therapeutic doses. The tone of the smooth muscle of the vessels is also greatly reduced. In addition, a strong muscular-spasmolytic action is manifested in the smooth muscle of the stomach, the intestinal tract, the urogenital tract and the respiratory system. Finally, there is some evidence that the compounds influence the cholesterol level and lipid level of the blood. These effects complement one another and the compounds are thus highly desirable as pharmaceutical agents to be used in the treatment of hypertension and conditions characterized by a constriction of the coronary blood vessels.

Pharmaceutical compositions for effecting such treatment will contain a major or minor amount, e.g. from 0.1 to 99.5 percent, preferably from 0.5 to 90 percent, of at least one compound of the invention in combination with a pharmaceutical carrier, the carrier comprising one or more solid, semi-solid or liquid diluent, filler and formulation adjuvant which is non-toxic, inert and pharmaceutically acceptable. salt pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 0.001 to about 10 mg/kg, preferably 0.002 to 1 mg/kg, when administered parenterally, and from about 0.05 to about 50 mg/kg, preferably 0.5 to 10 mg/kg, when administered orally. In some instances a sufficient therapeutic effect can be obtained at lower doses while in others, larger doses will be required. Administration is preferably parenterally or perorally, and more preferably by intravenous or perlingual routes.

Oral administration can be effected utilizing solid and liquid dosage unit forms such as powders, tablets, dragees, capsules, granulates, suspensions, solution, and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, an the like can also be added.

Where appropriate, dosage unit formulations for oral administration can be microencapsulated. The formulation can also be prepared to prolong or sustain the release as, for example, by coating or embedding particulate material in polymers, wax, or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents sterilized and sealed. An accompanying vial or vehicle can be provided for mixing prior to administration. Non-toxic salts and salt solutions can be added to render the injection isotonic. Stabilizers, preservatives and emulsifiers can also be added.

The following Examples will serve to further typify the nature of the present invention through the presentation of specific embodiments. These Examples should not be construed as a limitation on the scope of the invention since the subject matter regarded as the invention is set forth in the appended claims.

EXAMPLE 1

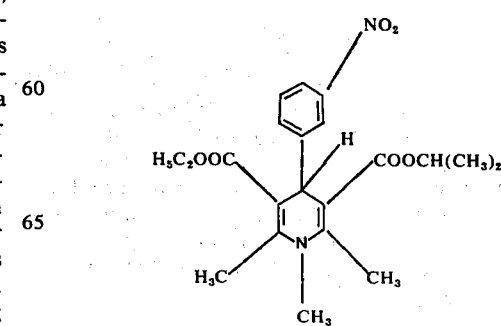

1,2,6-trimethyl-4-(3'-nitrophenyl)-1,4-dihydropyridine-3,5-dicarboxylic acid 3-methyl-ester-5-ethyl-ester of melting point 100°C (ethyl acetate/petroleum ether) was obtained by boiling a solution of 24.9g of 3'-nitrobenzylideneacetoacetic acid methyl ester and 14.3g of N-methylaminocrotonic acid ethyl ester in 150 ml of glacial acetic acid for 8 hours. Yield 49 percent of theory.

EXAMPLE 2

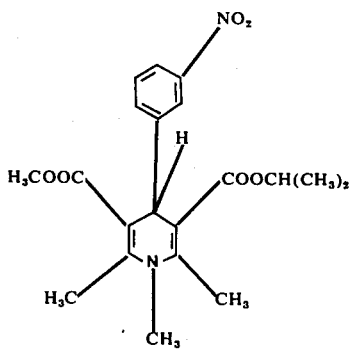

After heating a solution of 24.9g of 3'-nitrobenzylideneacetoacetic acid methyl ester, 14.4g of acetoacetic acid isopropyl ester and 7.0g of methylamine hydrochloride in 150 ml of pyridine for 4 hours, 1,2,6-trimethyl-4-(3'-nitrophenyl)-1,4-dihydropyridine-3,5-dicarboxylic acid 3-methyl-ester-5-isopropyl-ester of melting point 108°–109°C (from alcohol) was obtained. Yield 59 percent of theory.

EXAMPLE 3 (Process Variant b)

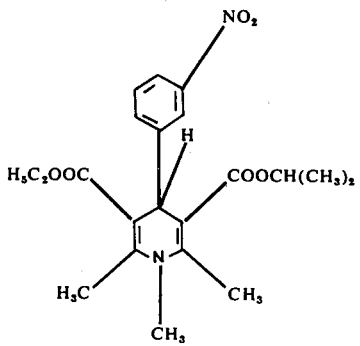

1,2,6-trimethyl-4-(3'-nitrophenyl)-1,4-dihydropyridine-3,5-dicarboxylic acid 3-ethyl-ester-5-isopropyl-ester of melting point 100°–101°C (ethanol) was obtained by boiling a solution of 7.6g of 3-nitrobenzaldehyde, 7.2g of acetoacetic acid isopropyl ester and 7.2g of N-methylaminocrotonic acid ethyl ester in 150 ml of ethanol/glacial acetic acid (2:3) for 6 hours. Yield 47 percent of theory.

EXAMPLE 4

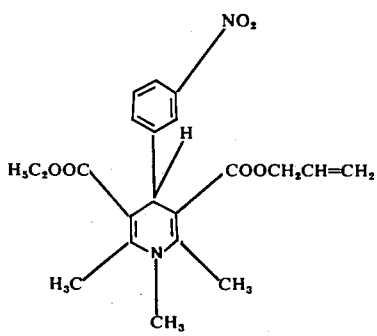

After boiling a solution of 26.3g of 3'-nitrobenzylideneacetoacetic acid ethyl ester and 14.2g of acetoacetic acid allyl ester and 7.0g of methylamine hydrochloride in 200 ml of pyridine for 6 hours, 1,2,6-trimethyl-4-(3'-nitrophenyl)-1,4-dihydropyridine-3,5-dicarboxylic acid 3-ethyl-ester-5-allylester of melting point 65°C (ether/petroleum ether) was obtained. Yield 38 percent of theory.

EXAMPLE 5

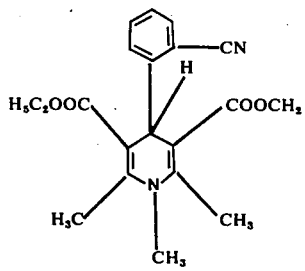

After boiling a solution of 24.3g of 2'-cyanobenzylideneacetoacetic acid ethyl ester, 11.6g of acetoacetic acid methyl ester and 7.0g of methylamine hydrochloride in 100 ml of pyridine for 4 hours, 1,2,6-trimethyl-4-(2'-cyanophenyl)-1,4-dihydropyridine-3,5-dicarboxylic acid 3-methyl-ester-5-ethyl-ester of melting point 175°C (ethanol) was obtained. Yield 61 percent of theory.

EXAMPLE 6

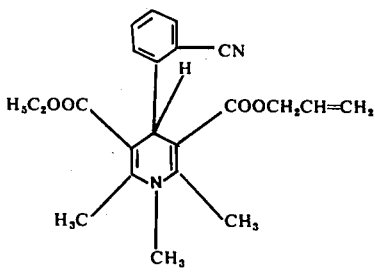

After boiling a solution of 12.2g of 2'-cyanobenzylideneacetoacetic acid ethyl ester, 7.2g of acetoacetic acid allyl ester and 4g of methylamine hydrochloride in 80 ml of pyridine for 2 hours, 1,2,6-trimethyl-4-

(2'-cyanophenyl)-1,4-dihydropyridine-3,5-dicarboxylic acid 3-ethyl-ester-5-allyl-ester of melting point 103°–104°C (ethyl acetate/petroleum ether) was obtained. Yield 46 percent of theory.

EXAMPLE 7

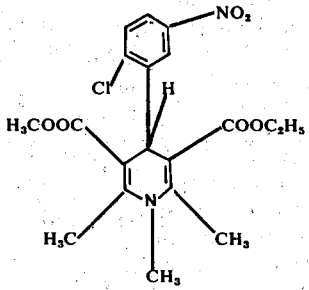

1,2,6-trimethyl-4-(6'-chloro-3'-nitrophenyl)-1,4-dihydropyridine-3,5-dicarboxylic acid 3-ethyl-ester-5-methyl-ester of melting point 164°C was obtained by heating a solution of 14.2g of 6'-chloro-3'-nitrobenzylideneacetoacetic acid methyl ester, 6.5g of acetoacetic acid ethyl ester and 4g of methylamine hydrochloride in 100 ml of pyridine for 4 hours. Yield 57 percent of theory.

EXAMPLE 8

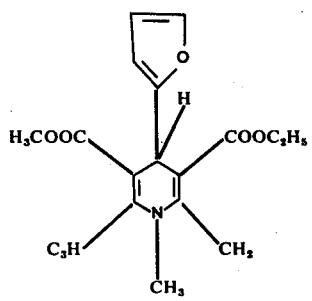

After boiling a solution of 10.4g of 2'-furfurylideneacetoacetic acid ethyl ester, 5.8g of acetoacetic acid methyl ester and 4g of methylamine hydrochloride in 100 ml of pyridine for 5 hours, 1,2,6-trimethyl-4-(furyl-2')-1,4-dihydropyridine-3,5-dicarboxylic acid 3-methyl-ester-5-ethyl-ester of melting point 103°C (ethyl acetate/petroleum ether) was obtained. Yield 61 percent of theory.

EXAMPLE 9

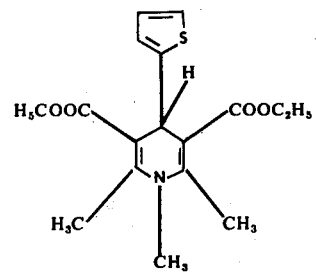

After heating a solution of 22.2g (2'-thenylidene)-acetoacetic acid ethyl ester, 11.6g acetoacetic acid methyl ester and 7.0g methylamine hydrochloride in 150 ml pyridine for 6 hours, 1,2,6-trimethyl-4-(2'-thienyl)-3,5-dicarboxylic acid 3-methyl ester 5-ethyl ester of melting point 113°C (ether) was obtained. Yield 59 percent of theory.

EXAMPLE 10

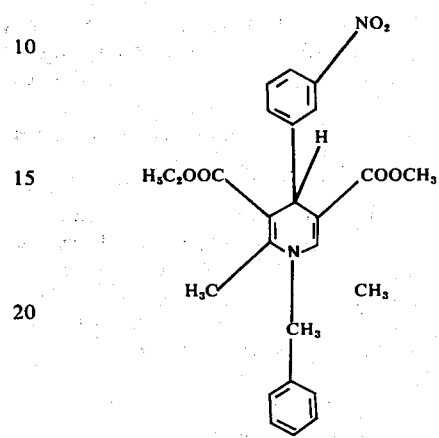

After heating a solution of 24.9g 3'-nitrobenzylideneacetoacetic acid methyl ester, 1.30g acetoacetic acid ethyl ester and 15.0g benzylamine hydrochloride in 200 ml pyridine for 6 hours, 1-benzyl-2,6-dimethyl-4-(3'-nitrophenyl)-1,4-dihydropyridine-3,5-dicarboxylic acid 3-methyl ester 5-ethyl ester of melting point 107°C (ether) was obtained. Yield 62 percent of theory.

EXAMPLE 11

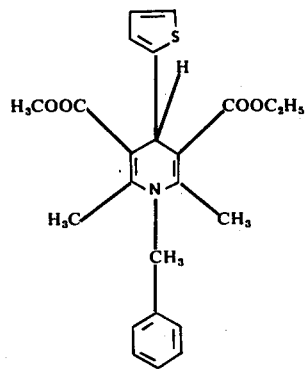

After boiling a solution of 22.2g of (2'-thenylidene)-acetoacetic acid ethyl ester, 11.6g acetoacetic acid methyl ester and 15.0g benzylamine hydrochloride in 150 ml pyridine for 6 hours, 1-benzyl-2,6-dimethyl-4-(2'-thienyl)-1,4-dihydropyridine-3,5-dicarboxylic acid 3-methyl ester 5-ethyl ester of melting point 113°C (ether) were obtained. Yield 49 percent of theory.

What is claimed is:
1. A compound of the general formula:

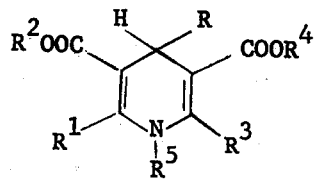

in which
R is thienyl or furyl, unsubstituted or substituted by lower alkyl, lower alkoxy or halo;
$R^1$ and $R^3$, independent of the other, is hydrogen methyl, ethyl or propyl;
$R^2$ and $R^4$ are different from one another and are lower alkyl, lower alkenyl, lower alkynyl, lower alkoxy(lower alkyl) or cycloalkyl of 3 to 6 carbon atoms, unsubstituted or substituted by hydroxy;
$R^5$ is lower alkyl or benzyl, or a pharmaceutically acceptable acid addition salt thereof.

2. The compound according to claim 1, in which R is thienyl or furyl, unsubstituted or substituted by alkyl of 1 to 4 carbon atoms, alkoxy of 1 to 4 carbon atoms, chloro or bromo.

3. The compound according to claim 1, in which $R^2$ and $R^4$ are different from one another and are alkyl of 1 to 4 carbon atoms, alkenyl of 2 to 4 carbon atoms, alkynyl of 2 to 4 carbon atoms, alkoxy (lower alkyl) with 1 to 4 carbon atoms in each of said alkoxy and alkyl or cyclohexyl, unsubstituted or substituted by hydroxy.

4. The compound according to claim 1, in which $R^5$ is alkyl of 1 to 4 carbon atoms or benzyl.

5. The compound according to claim 1, which is 1,2,6-trimethyl-4-(furyl-2')-1,4-dihydropyridine-3,5-dicarboxylic acid 3-methyl-ester-5-ethyl-ester.

6. The compound according to claim 1, which is 1-benzyl-2,6-dimethyl-4-(furyl-2')-1,4-dihydropyridine-3,5-dicarboxylic acid 3-methyl-ester-5-isopropyl-ester.

7. The compound according to claim 1, which is 1,2,6-trimethyl-4-(2'-thienyl)-3,5-dicarboxylic acid 3-methyl ester 5-ethyl ester.

8. The compound according to claim 1, which is 1-benzyl-2,6-dimethyl-4-(2'-thienyl)-1,4-dihydropyridine-3,5-dicarboxylic acid 3-methyl ester 5-ethyl ester.

9. The compound according to claim 1 which is 1-isopropyl-2,6-dimethyl-4-(thienyl-2')-3-carbomethoxy-5-carboethoxy-1,4-dihydropyridine.

10. The compound according to claim 1 which is 1,2,6-trimethyl-4-(furyl-2')-3-carboisopropoxy-5-carbo-$\beta$-propoxyethoxy-1,4-dihydropyridine.

11. The compound according to claim 1 which is 1,2,6-trimethyl-4-(furyl-2')-3-carboethoxy-5-carboisopropoxy-1,4-dihydropyridine.

* * * * *